United States Patent [19]

Luzzi et al.

[11] 4,228,162

[45] Oct. 14, 1980

[54] DIMETHYL ISOSORBIDE IN LIQUID FORMULATION OF ASPIRIN

[75] Inventors: Louis A. Luzzi; Joseph K. H. Ma, both of Morgantown, W. Va.

[73] Assignee: Research Corporation, New York, N.Y.

[21] Appl. No.: 55,703

[22] Filed: Jul. 9, 1979

[51] Int. Cl.² .................. A61K 31/60; A61K 31/605; A61K 31/62
[52] U.S. Cl. .................................. 424/232; 424/230; 424/235
[58] Field of Search ................................ 424/230, 235

[56] References Cited

U.S. PATENT DOCUMENTS

| | | | |
|---|---|---|---|
| 3,219,529 | 11/1965 | Nash et al. | 424/227 |
| 3,699,230 | 10/1972 | Beauchamp, Jr. | 424/274 |
| 4,082,881 | 4/1978 | Chen et al. | 424/241 |

*Primary Examiner*—Stanley J. Friedman
*Attorney, Agent, or Firm*—Oblon, Fisher, Spivak, McClelland & Maier

[57] ABSTRACT

A stabilized aspirin composition has been found which is comprised of acetylsalicylic acid and dimethyl isosorbide.

5 Claims, 6 Drawing Figures

DIMETHYL ISOSORBIDE IN LIQUID FORMULATION OF ASPIRIN

BACKGROUND OF THE INVENTION

1. Field of the Invention

This invention relates to a method of stabilizing acetylsalicylic acid compositions. More particularly, it relates to a stabilized acetylsalicylic acid composition with dimethyl isosorbide.

2. Description of the Prior Art

Aspirin, which exhibits a unique combination of effects on anti-inflammatory antipyretic, and analgesic treatments, is perhaps the most popular and effective non-prescription analgesic drug. However, it has been cautioned that aspirin ingestion can cause severe gastrointestinal bleeding in users and particularly, in patients with gastrointestinal lesions (P. R. Holt, *Proc. Soc. Exp. Biol. Med.*, 102, 517 (1959); P. H. N. Wood, S. E. A. Harvey, and A. Dixon, *Brit, Med. J.*, 1, 669 (1962); M. I. Grossman, K. K. Matsumote, and R. J. Lichter, Gastroenterology, 40, 383 (1961)). Although the mechanism by which the blood is lost is still unclear, studies (J. R. Leonards and G. Levy, *J. Pharm. Sci.*, 58, 1277 (1969); and A. Weiss, E. R. Pitman, and E. C. Graham, *Amer. J. Med.*, 31, 266 (1961)), have shown that aspirin, when given orally in a liquid form or when given intravenously, produces no occult bleeding. On the other hand, aspirin tablets are found to cause gastric bleeding particularly when tablets disintegrate slowly and remain in the stomach as large tablet fragments. These results suggest that the gastric irritation by aspirin may be greatly reduced by reducing the particle size of the drug. The reduction of the drug particle size in the gastrointestinal fluid may be best achieved by using a liquid dosage form. Hence, many attempts have been made to formulate a stable aspirin solution to reduce the undesirable side effect (H. R. Mehta and F. G. Drommond, *J. Amer. Phar. Assoc. Pract. Ed.*, 15, 103 (1954); H. W. Tomski and L. S.Waller, *Pharm. J.*, 144, 53 (1940); M. Farges, U.S. Pat. No. 3,316,150, Feb. 26, 1964; L. A. Luzzi, C. W. Whitworth, and H. W. Jun, *J. Pharm. Sci.*, 62, 1184 (1973); and T. W. Schwarz, N. G. Shvemar, and R. G. Renaldi, *J. Amer. Pharm. Assoc. Pract. Ed.*, 19, 40 (1958)).

The preparation of a stable liquid formulation of aspirin has become a classical pharmaceutical problem because of the instability of aspirin in various solvents. In aqueous solutions or in solvents containing water moisture, aspirin is notoriously unstable. The degradation has been known to be due to the hydrolysis of aspirin into salicylic acid and acetic acid. Studies (L. J. Edward, *Trans. Faraday Soc.*, 46, 723 (1956), also *Trans. Faraday Soc.*, 48, 696 (1952)), show that the hydrolysis follows first order kinetics and is subject to acid and base catalysis. Because of the rapid hydrolysis of aspirin in aqueous media, the attempts of liquid formulation of aspirin have been limited to the use of some non-aqueous solvents such as propylene glycol (H. R. Mehta and F. G. Drommond, *J. Amer. Pharm. Assoc. Pract. Ed.*, 15, 103 (1954)), ethyl alcohol (H. W. Tomski and L. S. Waller, *Pharm. J.*, 144, 53 (1940)), glycerol (M. Farges, U.S. Pat. No. 3,316,150, Feb. 26, 1964, and polyethylene glycol (T. W. Schwarz, N. G. Shvemar, and R. G. Renaldi, *J. Amer. Pharm. Assoc. Pract. Ed.*, 19, 40 (1958)). However, in addition to the solubility and hydrolysis (due to traces of moisture) problems that may be inherited in the use of these solvents, the formulations may also have to confront with another form of aspirin degradation as suggested by the study of Jun et al (H. W. Jun, C. W. Whitworth, and L. A. Luzzi, *J. Pharm. Sci.*, 61, (1972)). In this study, it was reported that aspirin undergoes trans-esterification with polyethylene glycol-400 to form salicylic acid and acetylated polyethylene glycol under prolonged storage. Although similar reactions have not been reported for the other hydroxyl solvents, it does not preclude the possibility of aspirin degradation via trans-esterification under long term storage. To circumvent the aspirin degradation, Luzzi and co-workers (L. A. Luzzi, C. W. Whitworth, and H. W. Jun, U.S. Pat. No. 3,842,170, Oct. 15, 1974) have proposed the use of esterified polyethylene glycol in the liquid formulation of aspirin.

In the past, attempts have been made to solubilize acetylsalicylic acid or to convert it to a fluid form in order to render acetylsalicylic acid compositions more palatable. This is particularly important for those people who find it difficult to consume tablets containing acetylsalicylic acid. Also, the administration of acetylsalicylic acid in pediatric practice is often difficult when tablets have to be sectioned in halves or quarters in order to provide the proper dosage of the drug for children. Thus, a need has existed for fluid compositions of acetylsalicylic acid for the accurate and convenient administration of the drug.

It has been known that in various pharmaceutical dosage forms, especially the liquid dosage forms, acetylsalicylic acid undergoes decomposition in the presence of water, aqueous or monohydroxy alcoholic solutions to salicylic acid and acetic acid. Several attempts have been made to formulate stable fluid solutions or suspensions of acetylsalicylic acid in a solvent mixture of high proof ethyl alcohol and high test anhydrous glycerin (U.S. Pat. No. 1,787,924) and in glycerin and propylene glycol solvents (U.S. Pat. No. 3,316,150 and British Pat. No. 1,147,348). In addition, polyethylene glycol suppository bases have been formulated which may contain acetylsalicylic acid or other medicinal agents (U.S. Pat. No. 2,975,099). However, it has been found that significant decomposition of acetylsalicylic acid still occurs in polyhydric alcohol bases despite the apparent absense of water. This factor is not as important as the hydrolytic effect water has on acetylsalicylic acid, but it is a significant factor when the "shelf-life" of anhydrous polyhydric alcohol-acetylsalicylic acid compositions is involved. The prior art has sought a solution to the problem of deterioration of acetylsalicylic acid by forming compositions of acid in polyhydric alcohol bases, but these attempts have only been partially successful. It has been shown that the decomposition of acetylsalicylic acid in apparently anhydrous polyhydric alcohols occurs via a transesterification reaction in which salicylic acid and acetylated polyhydric alcohol are produced. Specifically, the decomposition of acetylsalicylic acid has been shown to occur via a transesterification reaction with a polyethylene glycol base to produce salicylic acid and polyethylene glycol acetate. To circumvent this problem, (U.S. Pat. No. 3,842,170) esterified polyethylene glycol has been used in the liquid formulation of aspirin, however, this has not proved to be effective as problems with toxicity and pernicious, unpleasant taste has been noted.

Dimethyl isosorbide has been used as a solvent carrier for various pharmaceuticals, e.g., (U.S. Pat. No. 3,699,230) muscle relaxing drugs, wherein an additive synergistic effect has been noted, and (U.S. Pat. No. 4,082,881) various steroids when used in the form of an ointment, cream, lotion or parenteral liquid, such as eye drops, etc.

A need, therefore exists for acetylsalicylic compositions in which decomposition of the acid by hydrolysis and by transesterification is avoided. In particular, a need exists for fluid compositions of acetylsalicylic acid which are stable to decomposition via hydrolysis and transesterification.

SUMMARY OF THE INVENTION

Accordingly, one object of the invention is to provide stable dimethyl isosorbide based compositions of acetylsalicylic acid in which decomposition of the acid via hydrolysis and transesterification is avoided.

Another object of the invention is to provide stable fluid solutions of acetylsalicylic acid in which hydrolysis and transesterification of the acid is avoided by the use of dimethyl isosorbide.

Briefly, these and other objects of the invention, as hereinafter will become readily apparent, can be attained by pharmaceutical preparation which comprises acetylsalicylic acid (aspirin) and a carrier consisting essentially of dimethylisosorbide.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

We use dimethyl isosorbide (DMI) as the vehicle for the liquid formulation of aspirin. DMI has the following structure:

Preliminary studies indicate that this solvent is practically nontoxic. The fact that DMI is totally water miscible also suggests that this solvent is ideal for internal use. When used internally, it is predicted that DMI will be metabolized to form isosorbide, a remedy for diuretic purposes. From the chemical structural point of view, it is seen that DMI is practically inert to aspirin degradation.

It is known that fluid acetylsalicylic acid will decompose in water, aqueous and monohydroxy alcoholic solutions, and apparently anhydrous polyhydric alcohols, such as polyethylene glycol. The fact that the decomposition of the acid is not caused by the presence of extraneous amounts of water is confirmed by the absence of acetic acid, which would be present if the degradation was a result of hydrolysis. The absence of acetic acid has been confirmed by the lack of methyl group absorption of acetic acid in the nmr spectrum of a solution of acetylsalicylic acid in various apparently anhydrous polyhydric alcohols. It has been discovered that the decomposition of acetylsalicylic acid occurs by transesterification of the acid with the polyhydric alcohol as well as by hydrolysis due to the presence of water. This transesterification mode of decomposition was confirmed by the appearance of the methyl protons of the acetate moiety of polyhydric alcohol acetate in the nmr spectrum of aged samples of acetylsalicylic acid in various polyhydric alcohols. The supposed absorption of the methyl protons of the acetate moiety of the polyhydric alcohol acetate was confirmed by the appearance of the same absorption pattern in a portion of an acetylsalicylic acid solution containing authentic samples of the polyhydric alcohol acetate, particularly of polyethylene glycol acetate.

Figure 1:
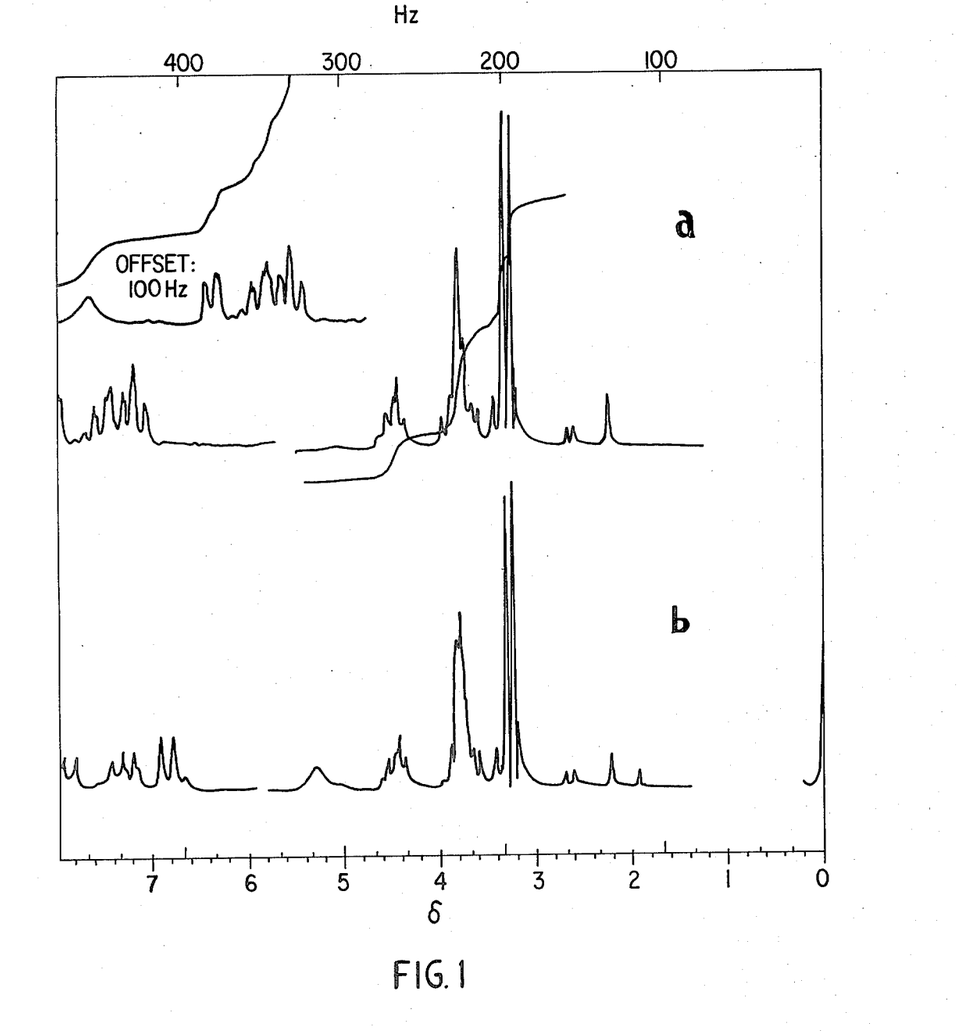
FIG. 1—NMR spectra in 1 M aspirin in dimethyl isosorbide in the absence (a) and presence (b) of 10%, v/v water. Spectrum (b) was taken after the sample was stored at 70° for 96 hours.
Figure 2:
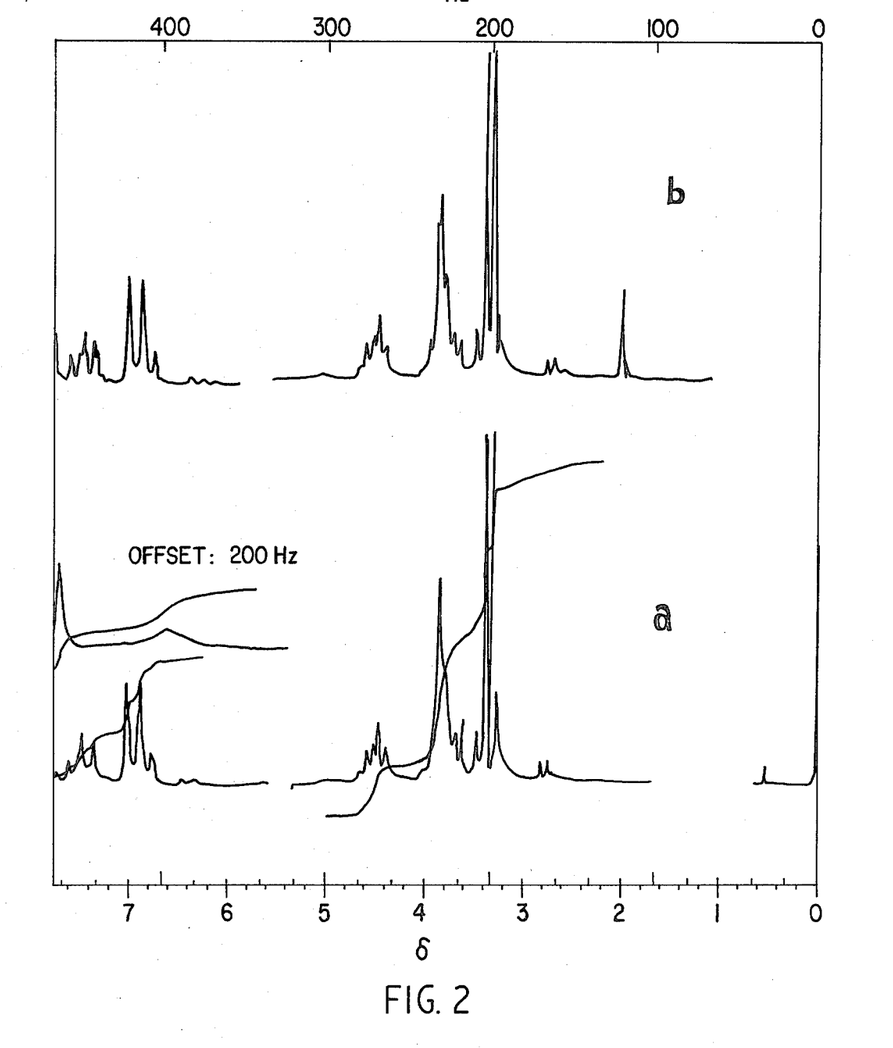
FIG. 2—NMR spectra of 1 M salicylic acid in dimethyl isosorbide in the absence (a) and presence (b) of acetic acid.

Nuclear magnetic resonance (nmr) spectroscopy was used to evaluate any possible interactions between aspirin and dimethyl isosorbide. FIG. 1 shows the nmr spectra of 1 M aspirin in dimethyl isosorbide in the absence (a) and presence (b) of 10% (v/v) of added water. The samples were prepared using USP grade aspirin, which was dried at 110° before use. In spectrum (a), the proton signals of the aromatic ring system of aspirin are shown in the region $\delta 7$ to $\delta 8.1$. The signal at $\delta 9.3$ is assigned to the carboxylic proton of aspirin. The signals in the region $\delta 3.2$ to $\delta 4.7$ are due to the protons of the solvent, whereas the signal at $\delta 2.23$ is due to the acetyl protons of aspirin. When this sample was heated at 70° for 24 hours, no detectable change was found in the nmr spectrum. Spectrum b was taken after the sample (containing 10% water) was stored at 70° C. for 96 hours. It is seen that the signal of the carboxylic proton has disappeared due to water exchange, the signals for the aromatic ring system have been changed, the signals for the solvent remain unchanged, and that a new peak appears at $\delta 2$ accompanied by a decrease of the acetyl proton signal of aspirin. The spectral change is found to be due to the hydrolysis of aspirin into salicylic acid and acetic acid. The nmr spectra of salicylic acid in dimethyl isosorbide in the absence and presence of acetic acid are shown in FIGS. 2a and 2b. The proton signal of acetic acid in this solvent is at $\delta 2$, whereas the signals for the aromatic ring system of salicylic acid are in the region of $\delta 6.8$ to $\delta 8.0$. It is seen that these peaks are almost identical with the corresponding peaks found in FIG. 1b, where the aspirin is partially hydrolyzed into salicylic acid and acetic acid.

The results of the nmr studies show that dimethyl isosorbide does not interact chemically with aspirin, not does it induce the degradation of aspirin. The only route of aspirin degradation is via hydrolysis which is inevitable when water is present in the system.

The liquid formulations of aspirin should contain a pharmaceutically effective concentration of acetylsalicylic acid, preferably up to 280 mg/ml of dimethyl isosorbide, more preferably 10–180 mg/ml.

The solubility of aspirin in propylene glycol, polyethylene glycol-400, and dimethyl isosorbide was determined as follows: 3 grams of aspirin was placed into a screw capped bottle containing 10 ml of one of the above solvents. The bottle was constantly shaken at room temperature for 24 hours. The solution was then filtered for analysis. The determination of aspirin contents in the solubility samples was carried out using a fluorometric technique, in which the aspirin was completely hydrolyzed into salicylic acid, and the fluorescence of salicylic acid was then measured. The concentration of salicylic acid in the samples was determined based on a fluorescence calibration curve of known concentrations of salicylic acid in the range of $5 \times 10^{-7}$ M to $5 \times 10^{-6}$ M. The concentration of salicylic acid so determined was then converted to the concentration of aspirin. The solubility of aspirin in various solvents is expressed in mg/ml. The samples were treated as follows: The hydrolysis of aspirin was achieved by transferring 2.5 µl of the filtered sample into a 25 ml volumetric flask containing 0.5 ml of a 1 N NaOH solution. After 30 minutes, when the hydrolysis was complete, 0.5 ml of a 1 N HCl was added to the flask to neutralize the excess sodium hydroxide. The solution was then diluted with a pH 7 phosphate buffer to 25 ml. For fluorescence measurement, 1, 2, 3, and 4 µl of the diluted solution were transferred into different fluorescence cuvettes containing 2 ml of pH 7 buffer. The fluorescence measured from these solutions was then used to determine the aspirin content in the solvents.

The solubility of aspirin in dimethyl isosorbide is found to be 280 mg/ml, whereas in propylene glycol and in polyethylene glycol-400, the solubilities are found to be 160 mg/ml and 254 mg/ml, respectively. These results show that dimethyl isosorbide is an excellent solvent for the liquid formulation of aspirin. An aspirin tablet usually contains 325 mg of aspirin. Using dimethyl isosorbide, the same strength may be formulated in less than 1.5 ml of solution. Liquid formulation may also enhance the absorption of the drug, and therefore, reduce the dose required to achieve the same effect. The advantage of using a high solubilizing solvent is that the amount of solvent taken may be reduced, and hence, the possible side effect of the solvent may also be reduced. From a stability point of view, the stability of aspirin in a solution increases with increasing concentrations of the drug. Thus, the use of dimethyl isosorbide which is capable of dissolving more aspirin than other solvents, should also enhance the stability of aspirin.

Other additives can be added to the aspirin-dimethyl isosorbide compositions such as flavoring agents, sweetening agents and other drugs. Suitable flavoring agents include vanilla, chocolate, cherry, grape and raspberry, etc. Suitable sweetening agents include sugars such as glucose, fructose, sucrose, sorbitol, and lactose; and artificial sweeteners such as saccharin, cyclamate, etc. Suitable drugs which may also be incorporated include propoxiphene, codeine, chlorpheneramine, pyrabenzamine or other analgesic and antihistaminic drugs. Also sedatives such as the barbituates and tranquilizers.

Toxicity information on dimethyl isosorbide was determined as follows:

Acute Oral Toxicity—Rat

An approximate oral LD50 of dimethyl isorbide was determined.

The acute oral (LD50) toxicity of DMI in rats is about 5.63 ml per kg of body weight (calculated according to the moving average method of Horn, H. J., Biometrics, 12; 311 (1956)). Groups of 5 rats were given the following dosages: 1.47, 2.15, 3.16, 4.64, 6.81 and 10.0 ml/kg, respectively. All of the 20 rats given the four low dosages survived, whereas all of the 10 rats given the two higher dosages died. Signs of intoxication consisted of depression, lacrimation, labored respiration, tachcardia and ataxia. Cross examination of the tissues of the animals that died revealed hyperemic lungs, slight irritation of the small intestine and congestion of kidneys and adrenals.

In accordance with the classification for acute oral toxicities as proposed by Hodge, H. C. and Sterner, J. H., (*American Industrial Hygiene Association Quarterly*, 10: (4) 93 (December 1949)), DMI would be considered as "practically nontoxic."

Acute Percutaneous Toxicity—Rabbit

The acute percutaneous toxicity of undiluted dimethyl isosorbide when maintained in contact with rabbit skin was also determined.

The acute percutaneous toxicity of undiluted DMI, when maintained in contact with the rabbit skin under a cover of rubber dental dam for 24 hours, is greater than 10 ml per kg of body weight. Groups of four albino rabbits were given dosages of 1.00, 2.15, 4.64 and 10.0 ml per kg, respectively. All rabbits survived. Under these conditions, there was transitory mild to moderate erythema. No gross pathological findings were noted when the rabbits were sacrificed.

Skin Irritation—Rabbit

Dimethyl isosorbide undiluted, and in concentrations of 80%, 60% and 20% (w/v) in water, was tested on rabbits.

No score (edema or erythema) was obtained on any of the rabbits at either 24 or 72 hours. Therefore, the primary irritation index (P.I.I.) was zero for each sample.

Additional tests were similarly done on rabbit skin. On this occasion the P.I.I. was 0.083. Of 24 readings, each of which had a potential of 8, only one had a score of 1.0.

Eye Irritation—Rabbit

Dimethyl ether was instilled into the conjunctival sac of the rabbit eye.

Over a period of several years two different lots of DMI (designated here merely as A or B) were tested at different times and at various concentrations. The results obtained for the particular test for the specified concentration are provided in Table I.

TABLE I

| Conc. (%) | Lot | No. of Test | Condition of Eyes | Average Score[1] at Time Stated |||||| 
|---|---|---|---|---|---|---|---|---|---|
| | | Eyes | | 1 hour | 24 hours | 48 hours | 72 hours | 96 hours | 7 days |
| 100 | A | 1 | 6[2] | Unwashed | 0.0 | 15.0 | 10.3 | 10.0 | 10.0 | 10.0 |
| 100 | A | 2 | 6 | Unwashed | 0.0 | 0.0 | 0.0 | 0.0 | 0.0 | 0.0 |

TABLE I-continued

| Conc. (%) | Lot | Test | No. of Eyes | Condition of Eyes | Average Score[1] at Time Stated | | | | | |
|---|---|---|---|---|---|---|---|---|---|---|
| | | | | | 1 hour | 24 hours | 48 hours | 72 hours | 96 hours | 7 days |
| 100 | B | 1 | 6[3] | Unwashed | 3.7 | 11.3 | 5.6 | 5.0 | 5.0 | 4.6 |
| 100 | A | 1 | 3 | Washed 2 sec. | 0.0 | 0.0 | 0.0 | 0.0 | 0.0 | 0.0 |
| 100 | A | 2 | 3 | Washed 2 sec. | 0.0 | 0.0 | 0.0 | 0.0 | 0.0 | 0.0 |
| 100 | B | 1 | 3 | Washed 2 sec. | 2.7 | 18.0 | 17.3 | 9.4 | 8.7 | 0.0 |
| 80 | A | 1 | 6 | Unwashed | 0.0 | 0.0 | 0.0 | 0.0 | 0.0 | 0.0 |
| 80 | A | 1 | 3 | Washed 2 sec. | 0.0 | 0.0 | 0.0 | 0.0 | 0.0 | 0.0 |
| 60 | A | 1 | 6 | Unwashed | 0.0 | 0.0 | 0.0 | 0.0 | 0.0 | 0.0 |
| 60 | A | 1 | 3 | Washed 2 sec. | 0.0 | 0.0 | 0.0 | 0.0 | 0.0 | 0.0 |
| 40 | A | 1 | 6 | Unwashed | 0.0 | 0.0 | 0.0 | 0.0 | 0.0 | 0.0 |
| 40 | A | 1 | 3 | Washed 2 sec. | 0.0 | 0.0 | 0.0 | 0.0 | 0.0 | 0.0 |

[1] Out of a potential score of 100 at each reading.
[2] One eye had a consistent score of 60-64, no other eye had a score greater than 14 at any reading, one eye was also scored zero.
[3] One eye was consistently scored at 28-30 and one other eye was always scored zero.

The data of Table I indicate considerable variability in the response of individual rabbit eyes to the undiluted DMI. The following classification of degree of irritancy, according to the terminology of Kay and Calandra, was made for the various tests on the unwashed eye:

| Conc. (%) | Lot | Test | Classification (Kay and Calandra) |
|---|---|---|---|
| 100 | A | 1 | Cannot be classified[a] |
| 100 | A | 2 | Nonirritating |
| 100 | B | 1 | Mildly irritating |
| 80 | A | 1 | Nonirritating |
| 60 | A | 1 | Nonirritating |
| 40 | A | 1 | Nonirritating |

[a] Because of deviation on one eye which had scores of 60-64, this test did not meet arbitrary criteria that 40% of individual scores equal mean average score plus or minus 5 points.

The classification of DMI according to specifications provided in the Federal Hazardous Substances Act for the specified test and concentration are shown below:

| Conc. (%) | Lot | Test | No. of Eyes Positive No. of Eyes Tested CFR | Class. as Irritating Code of Federal Regulations |
|---|---|---|---|---|
| 100 | A | 1 | 4/6 | Positive |
| 100 | A | 2 | 0/6 | Negative |
| 100 | B | 1 | 0/6 | Negative |
| 80 | A | 1 | 0/6 | Negative |
| 60 | A | 1 | 0/6 | Negative |
| 40 | A | 1 | 0/6 | Negative |

Instillation into Rabbit Ear

DMI was introduced onto the external auditory canal of each of four right rabbit ears. Likewise, four other right rabbit ears were instilled with 0.35 ml of 40% DMI in water. No irritation to the integument of the external auditory canal was observed at any time or at 5 days when the rabbits were sacrificed and the entire canal dissected to the tympanum.

Human Patch Tests

Undiluted dimethyl ether of isosorbide has been tested under a closed patch of human subjects in accordance with the prophetic patch-test procedure originally designed by the dermatologist, B. Schwartz, M.D., and more recently adapted by R. B. Osbourn, M.D.

The results obtained were as follows:

| Product | Concentration | | No. of Reactors/ No. of Subj. Tested | | |
|---|---|---|---|---|---|
| | 1st Appl. | 2nd Appl. | 1st Appl. | 2nd Appl. | Both Appl. |
| Dimethyl Isosorbide | 100% | 100% | 0/200 | 2[a]/200 | 2/200 |

[a] Two subjects, each of whom had a questionable (1) reaction on the second application only, were immediately re-tested by application to another site by means of a semi-closed patch; both were negative 48 hours later when the patches were removed.

It was concluded that undiluted dimethyl isosorbide is neither a primary irritant to the human skin nor a skin sensitizer.

Having generally described this invention, a further understanding can be obtained by reference to certain specific examples which are provided herein for purposes of illustration only and are not intended to be limiting unless otherwise specified.

Six formulations (see Table II), each containing 180 mg/ml of USP grade aspirin, were prepared for the hydrolysis studies. No attempt of drying of the drug or the solvent was made prior to the experiment. 25 ml of each of the six formulations were placed in a screw capped bottle which was then kept in a temperature controlled water bath set at a designated temperature. Samples of each of the formulations were pipetted out at selected time intervals, and were immediately analyzed for salicylic acid content. The analysis of salicylic acid was carried out using the fluorometric method previously described. The samples were diluted 1000 times in a volumetric flask, a few μl's of the diluted samples were then transferred into a fluorescence cuvette containing 2 ml of pH 7 buffer for the fluorescence measurement. The hydrolysis studies were carried out at 40, 45, 50, 60 and 70° C. and at room temperature.

TABLE II

Formulations of Aspirin Solution in Dimethyl Isosorbide for the Stability Studies

| Formulation* | Water Content (%, V/V) | Flavoring Agent (4 drops/10ml) |
|---|---|---|
| A** | — | — |
| B | 1 | — |

TABLE II-continued

Formulations of Aspirin Solution in Dimethyl Isosorbide for the Stability Studies

| Formulation* | Water Content (%, V/V) | Flavoring Agent (4 drops/10ml) |
|---|---|---|
| C | 10 | — |
| D | — | Peppermint oil |
| E | — | Cinnamon oil |
| F | — | Spearmint oil |

*All solutions contain 180 mg/ml of USP grade aspirin.
**Both ASA and DMI were used without further purification.

The rate constant of aspirin hydrolysis was determined according to the following equation:

$$C = C_o e^{-kt} \quad (1)$$

where $C_o$ is the initial concentration of aspirin, C, the concentration of aspirin at time t, and k, the rate constant. For practical purposes, the above equation may be converted to $$\log 100 C/C_o = 2 - kt/2.303 \quad (2)$$

Thus, the plot of the log values of percentage aspirin remaining versus time gives a straight line with a slope of $-k/2.303$.

The rate constants determined at various temperatures were used to predict the aspirin degradation at room (25° C.) and refrigeration (5° C.) temperatures using the Arrhenius equation:

$$\log k = \log A - E_a/2.303 RT \quad (3)$$

where k is the rate constant at temperature T, A, a constant, R, the gas constant, and $E_a$, the activation energy of the reaction. A plot of log k versus 1/T should yield a straight line with the slope equal to $-E_a/2.303R$. For the same reaction, $E_a$ is a constant. From the plot, the rate constants at 25° and 5° can also be calculated. These constants can then be used for the prediction of the shelf life (time for 10% degradation) of the aspirin formulations at room and refrigeration temperatures.

Figure 3:
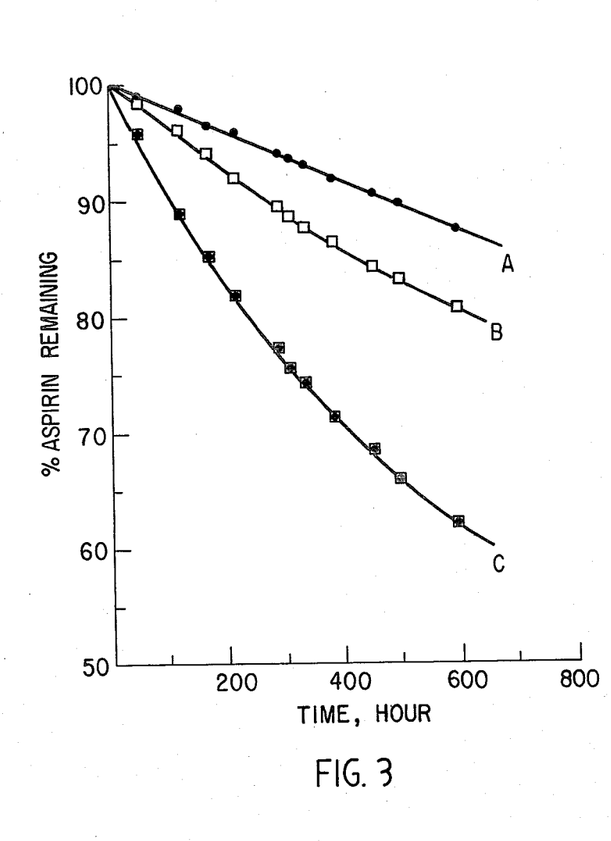
FIG. 3—The degradation of aspirin (180 mg/ml) in dimethyl isosorbide containing (A) 0%, (B) 1%, and (C) 10% of added water at 50° C.

The degradation of aspirin in formulations A, B, C at 50° C. are shown in FIG. 3. The data are presented as an example for the aspirin degradation at various temperatures. It is seen that even when there is no added water (formulation A), aspirin still undergoes degradation. The sample was periodically examined by nmr spectral measurement. It was found that the degradation is due to aspirin hydrolysis. This suggests that a certain amount of water is present in the formulation which may be from the USP grade aspirin (allows 0.5% weight loss on drying) and from the absorption of water by the solvent.

The results of FIG. 3 also suggest that the hydrolysis of aspirin follows second order kinetics, i.e., the reaction rate and its half-life are both dependent on both aspirin and water concentrations. For the sake of simplicity, the data of FIG. 3 and those obtained at various temperatures have been treated with equation 2, which is derived from first-order kinetics. The validity of this approach is based on the fact that for the first 50% of the reaction, the results obtained from the first order equation have little or no difference from those obtained from the second order equation. It should be pointed out, however, that the degradation of aspirin determined from equation 2 is slightly greater than the true degradation, and that the rate constant determined from the first order equation is not the true constant for the hydrolysis of aspirin.

Figure 4:
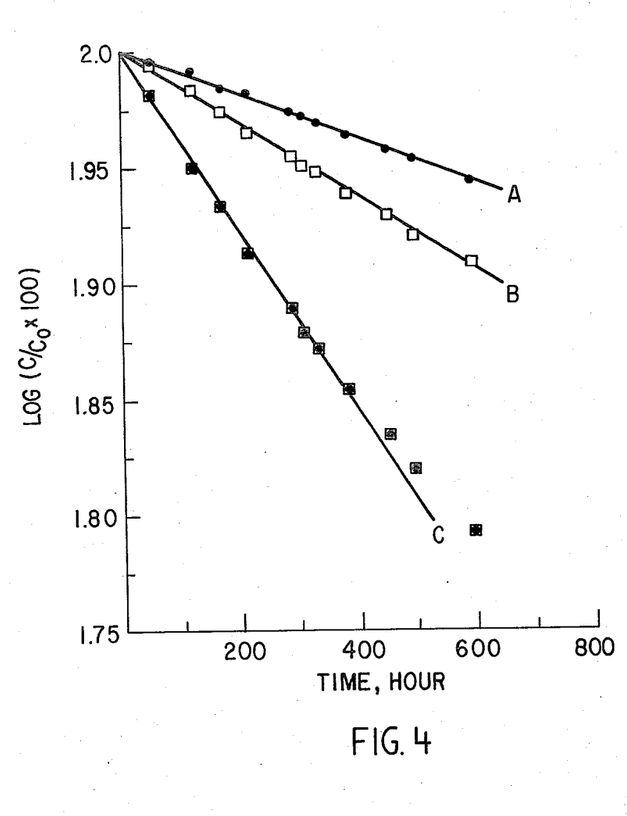
FIG. 4—Plots a log ($C/C_o \times 100$) vs. time for the degradation of aspirin in formulations A, B and C.

FIG. 4 shows the plots of equation 2 for the data shown in FIG. 3. From the slope of the plots the rate constant of aspirin degradation in formulations A, B, and C were determined. The values can be found in Table III, which also includes the rate constants obtained at other temperatures.

Figure 5:
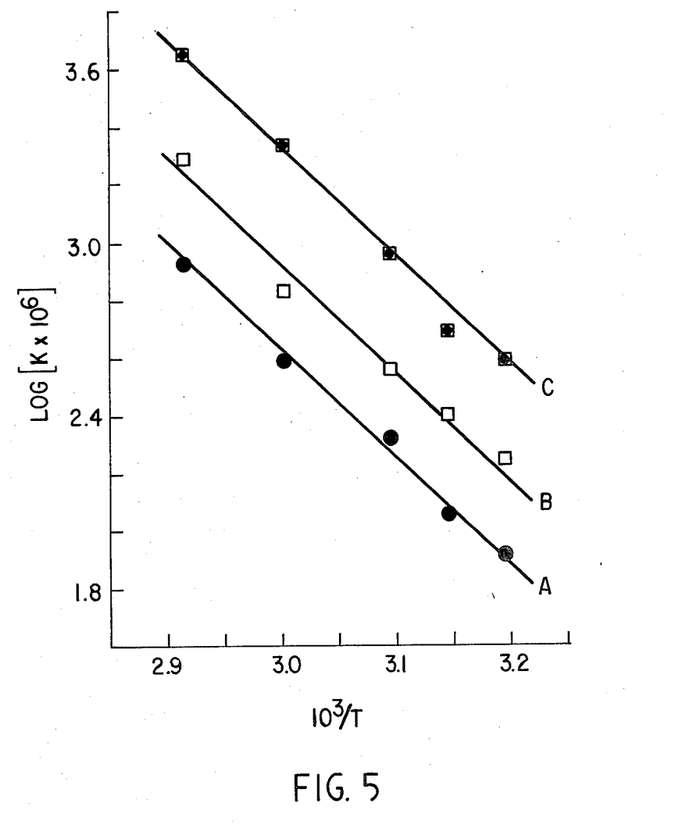
FIG. 5—Arrhenius plots of the degradation of aspirin in formulations A, B and C, at various temperatures.

FIG. 5 shows the relationship between rate constant and absolute temperature in formulations A, B and C. It is seen that the log value of the rate constant is linearly related to 1/T. This suggests that the aspirin degradation in these formulations follows the approximation of the Arrhenius equation. The fact that the three lines are parallel to one another also suggests that the degradation of aspirin in these formulations is due to a common reaction-hydrolysis. From the plots of FIG. 5, the rate constants of aspirin degradation in formulation A at 25° and 5° C. were calculated to be $19.05 \times 10^{-6}$ and $2.35 \times 10^{-6}$ hr.$^{-1}$, respectively. From these values, the shelf-life (time for 10% degradation) of formulation A were predicted to be 230 days at 25° C., and 62.5 months at 5° C.

The predicted value at 25° C. correlates well with the experimental results obtained at room temperature. The data obtained at room temperature are not sufficient for kinetic evaluations. But the results show that at the end of 30 days, about 1.5% of aspirin is degraded in formulations A, D, E and F. In solutions containing 1% and 10% of added water (formulations B and C), the degradation at the end of 30 days was found to be 2.8 and 4.8%, respectively.

Figure 6:
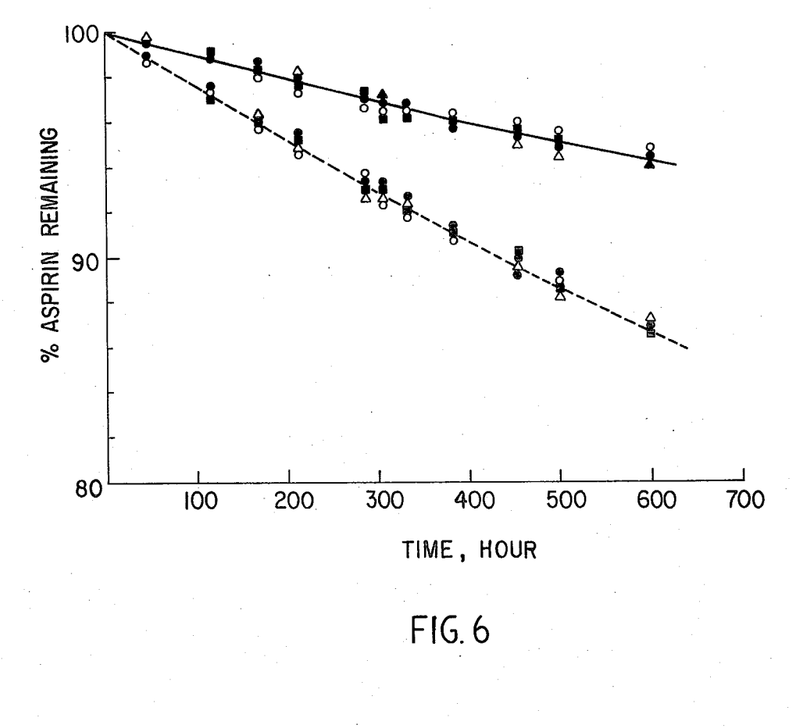
FIG. 6—The degradation of aspirin in formulations A (●), D (o), E (▲) and F (■) at 40° (—) and 50° (----).

FIG. 6 shows the degradation of aspirin in formulations A, D, E, and F, at 40° and 50° C. It is seen that the presence of peppermint oil, cinnamon oil, spearmint oil does not affect the stability in aspirin in dimethyl isosorbide. These samples were also examined with nmr spectroscopy which confirms that hydrolysis is the only cause for aspirin degradation in dimethyl isosorbide.

The comparison of aspirin stability in dimethyl isosorbide with those in propylene glycol and polyethylene glycol-400 (14) is shown in Table IV. It can be seen that aspirin is more stable in dimethyl isosorbide than in the other solvents. This may be explained as follows: The hydrolysis is a second order reaction, thus, the increase of the concentration of aspirin or the decrease of the concentration of water will reduce the degradation; aspirin may undergo transesterification in solvents such as propylene glycol and polyethylene glycol-400 as an additional route of degradation. It should be pointed out that the choice of solvent does not prevent the hydrolysis of aspirin if in fact the solvent is contaminated with moisture, but can prevent the degradation of aspirin by other routes. The hydrolysis may be greatly reduced by formulating aspirin in a high concentration and/or by reducing the water content in the drug and the solvent. Ideally, an anhydrous composition is used to prevent hydrolysis.

TABLE II

Rate constants of Aspirin Degradation in Dimethyl Isosorbide Measured at Various Temperatures.

| Temperature °C. | Rate Constant $\times 10^4$, hr$^{-1}$ | | |
|---|---|---|---|
| | Formulation A | Formulation B | Formulation C |
| 40 | 0.82 | 1.82 | 3.75 |
| 45 | 1.15 | 2.50 | 4.91 |
| 50 | 2.10 | 3.68 | 9.10 |
| 60 | 3.76 | 6.68 | 21.88 |

TABLE II-continued

Rate constants of Aspirin Degradation in Dimethyl Isosorbide Measured at Various Temperatures.

| Temperature °C. | Rate Constant × $10^4$, $hr^{-1}$ | | |
|---|---|---|---|
| | Formulation A | Formulation B | Formulation C |
| 70 | 8.44 | 19.60 | 45.10 |

TABLE IV

Comparison of Aspirin Stability in Dimethyl Isosorbide, Propylene Glycol, and Polyethylene Glycol-400.

| Solvent | Concentration of Aspirin | Time for 10% Degradation | |
|---|---|---|---|
| | | 25° C. | 5° C. |
| propylene glycol | 0.36 M | 151.2 days | 55.8 mos. |
| polyethylene glycol-400 | 0.36 M | 18.8 days | 2.90 mos. |
| dimethyl isosorbide | 1.00 M | 230 days | 62.5 mos. |

Having now fully described the invention it will be apparent to one of ordinary skill in the art that many changes and modifications can be made thereto without departing from the spirit or scope of the invention as set forth herein.

What is claimed as new and desired to be secured by Letters Patent is:

1. A stable liquid aspirin composition which comprises the admixture of a pharmaceutically effective concentration of acetylsalicylic acid in dimethyl isosorbide.

2. The composition of claim 1, wherein said acetylsalicylic acid is present in a concentration of up to 280 mg/ml of dimethyl isosorbide.

3. The composition of claim 2, wherein said acetylsalicylic acid is present in a concentration of 10–180 mg/ml of dimethyl isosorbide.

4. The composition of claim 1, wherein the composition is anhydrous.

5. The composition of claim 1, wherein the composition contains a flavoring agent.

* * * * *